US012648901B2

(12) United States Patent
Adamy et al.

(10) Patent No.: US 12,648,901 B2

(45) **Date of Patent: *Jun. 9, 2026**

(54) OIL IN WATER PERSONAL CARE EMULSIONS COMPRISING A SULFOSUCCINATE/LAURAMPHOACETATE SURFACTANT MIXTURE

(71) Applicant: SPECIALTY OPERATIONS FRANCE, Lyons (FR)

(72) Inventors: Monique Martine Françoise Adamy, Asnières-sur-seine (FR); Jennifer Jessika Cazette, Sucy-en-brie (FR)

(73) Assignee: SPECIALTY OPERATIONS FRANCE, Lyons (FR)

(*) Notice: Subject to any disclaimer, the term of this patent is extended or adjusted under 35 U.S.C. 154(b) by 0 days.

This patent is subject to a terminal disclaimer.

(21) Appl. No.: 18/762,754

(22) Filed: Jul. 3, 2024

(65) Prior Publication Data

US 2024/0366492 A1 Nov. 7, 2024

Related U.S. Application Data

(63) Continuation of application No. 16/075,789, filed as application No. PCT/EP2017/053539 on Feb. 16, 2017, now Pat. No. 12,059,488.

(60) Provisional application No. 62/295,773, filed on Feb. 16, 2016.

(30) Foreign Application Priority Data

Feb. 16, 2016 (EP) .................................... 16155947

(51) Int. Cl.

| | |
|---|---|
| ***C11D 1/94*** | (2006.01) |
| ***A61K 8/37*** | (2006.01) |
| ***A61K 8/46*** | (2006.01) |
| ***A61K 8/73*** | (2006.01) |
| ***A61Q 5/02*** | (2006.01) |

(52) U.S. Cl.

CPC ................ *A61K 8/737* (2013.01); *A61K 8/37* (2013.01); *A61K 8/466* (2013.01); *A61Q 5/02* (2013.01); *A61K 2800/30* (2013.01); *A61K 2800/596* (2013.01)

(58) Field of Classification Search

CPC .. C11D 1/88; C11D 1/94; C11D 1/002; C11D 17/0021; C11D 3/37

See application file for complete search history.

(56) References Cited

U.S. PATENT DOCUMENTS

| | | | | |
|---|---|---|---|---|
| 6,395,691 | B1 * | 5/2002 | Tsaur | C11D 17/0013 510/159 |
| 6,906,016 | B1 * | 6/2005 | Tsaur | A61K 8/732 510/462 |
| 9,271,908 | B2 | 3/2016 | Allef et al. | |
| 2003/0216501 | A1 | 11/2003 | Herve et al. | |
| 2010/0158830 | A1 | 6/2010 | Wei et al. | |
| 2011/0243873 | A1 | 10/2011 | Hough et al. | |
| 2012/0015893 | A1 | 1/2012 | Herrwerth et al. | |
| 2012/0134948 | A1 | 5/2012 | Springer et al. | |
| 2014/0301966 | A1 | 10/2014 | Hough et al. | |
| 2014/0349902 | A1 * | 11/2014 | Allef | A61Q 19/10 510/491 |
| 2014/0360522 | A1 | 12/2014 | Anderson | |
| 2015/0004112 | A1 | 1/2015 | Ritter et al. | |
| 2015/0044157 | A1 * | 2/2015 | Kulkarni | A61K 8/602 514/561 |
| 2015/0157548 | A1 | 6/2015 | De Feij et al. | |
| 2015/0297485 | A1 * | 10/2015 | Kleinen | A61K 8/4973 514/786 |
| 2015/0297489 | A1 | 10/2015 | Kleinen et al. | |
| 2016/0030325 | A1 | 2/2016 | Jerome et al. | |
| 2016/0045424 | A1 | 2/2016 | Schwab et al. | |

FOREIGN PATENT DOCUMENTS

WO 2010118925 A2 10/2010

* cited by examiner

*Primary Examiner* — Charles I Boyer

(74) *Attorney, Agent, or Firm* — Vorys, Sater, Seymour and Pease LLP; Maryellen Feehery Hank; Anthony P. Venturino

(57) ABSTRACT

The present invention relates to sulfate-free aqueous personal care composition comprising from about 0.2 pbw to about 15 pbw of a derivatized cationic guar comprising cationic substituent groups and non ionic substituent groups, at least 0.05 pbw of an oil and from about 2 pbw to about 20 pbw of a surfactant system comprising at least one lauramphoacetate, and one sulfosuccinate. It is also directed toward the use of such a composition for washing keratin substrates, in particular the hair or the scalp.

15 Claims, No Drawings

OIL IN WATER PERSONAL CARE EMULSIONS COMPRISING A SULFOSUCCINATE/LAURAMPHOACETATE SURFACTANT MIXTURE

This application is a continuation application of U.S. patent application Ser. No. 16/075,789 filed Aug. 6, 2018 which is a U.S. national phase entry under 35 U.S.C. § 371 of International Application No. PCT/EP2017/053539, filed on Feb. 16, 2017, which claims priority to U.S. provisional application No. 62/295,773 filed on Feb. 16, 2016 and to European application No. EP16155947 filed on Feb. 16, 2016, the whole content of each of these applications being incorporated herein by reference for all purposes.

The present invention relates to personal care compositions and methods for using such compositions.

At the present time, most of the commercially available personal care compositions are based on sulfate-containing surfactants such as sodium lauryl sulfate, (SLS), ammonium lauryl sulfate (ALS), sodium laureth sulfate (SLES) or ammonium laureth sulfate (ALES). SLS, ALS, SLES and ALES are the most widespread sulfate-containing surfactants used in this field as they are inexpensive and as they exhibit at the same time satisfactory cleansing and foaming properties. Another advantage is that they can be easily thickened by the addition of common salt such as sodium chloride.

However personal care compositions including sulfate-containing surfactants present also significant drawbacks. As a matter of fact sulfate-containing surfactants such as SLS are known to be liable to give rise to tolerance problems, especially on the skin and the eyes. Another drawback of sulfate-containing surfactants is their tendency to strip the skin, scalp or hair of its natural oils, fats or proteins contained at their surface. In the long term the repeated use of personal care compositions including sulfate-containing surfactants may therefore cause irritation to the skin or scalp and/or give damage on hair fibers.

In recent times there is thus an increasing demand for personal care compositions including safe, environment friendly, and/or milder surfactants, and especially for personal care compositions free of sulfate-containing surfactants.

One of the major challenges of formulating sulfate-free personal care compositions lies in the need to maintain mildness, satisfactory cleansing, conditioning and foaming properties without negatively impacting viscosity of the overall composition.

For instance, as far as hair care compositions such as shampoo formulations are concerned, an elevated viscosity is necessary for the usage under application conditions. As mentioned previously when sulfate-containing surfactants such as SLS or SLES are present in a composition viscosity can be increased relatively easily by the addition of small amounts of sodium chloride. However, this is generally not the case for anionic surfactants of the acetylated amino acid type, such as methyl cocoyl taurate. Even at very high salt concentrations aqueous solutions are still fluid and not usable for the targeted applications. On the other hand, non-ionic surfactants cannot be thickened at all by the addition of electrolytes. In a sulfate-free surfactant chassis the use of electrolytes such as sodium chloride is therefore not sufficient to provide compositions having an adequate viscosity for use as personal care cleansing compositions. Moreover, compositions involving the use of a thickener of gums, such as xanthan gum, are not always desirable since they have a structuring effect on the gel imparting elastic properties thereto which leads to the formation of thick lumps when drawing the composition out of the bottle.

It is thus an object of the present invention to address the ever increasing demand in the market for personal care compositions that are free of sulfate-containing surfactants without negatively affecting viscosity, foaming properties and conditioning on target area.

One of the aims of the present invention is therefore to provide personal care compositions that exhibit good foaming properties and conditioning on target area and that maintain a satisfactory viscosity, while at the same time being free of sulfate-containing surfactants.

The large majority of known personal care compositions which are free of sulfate-containing surfactants generally need, in order to obtain the foam volume and quality desired by consumers, to contain large amounts of other surfactants.

However, the use of large amounts of surfactants is undesirable of obvious reasons. On the one hand it necessarily increases the overall cost of the compositions. Increasing the amount of surfactants also generally increases on the other hand the risk to lead to tolerance problems.

This is the reason why there is a real need to provide sulfate-free personal care compositions that exhibit good foaming properties and conditioning on target area and that maintain a satisfactory viscosity, without having to use large amounts of surfactants.

The Applicant has now discovered that a personal care composition containing a particular combination of surfactants, one of which is lauramphoacetate and the another one of which is one sulfosuccinate, makes it possible to achieve the objectives outlined above, and especially improved oil deposition on target area, thus conditioning, when the personal care composition further contains a specific derivatized cationic guar.

The subject of the invention is thus a sulfate-free aqueous personal care composition comprising:

i) from about 0.2 pbw to about 15 pbw of a derivatized cationic guar comprising cationic substituent groups and non ionic substituent groups
ii) at least 0.05 pbw of an oil; and
iii) from about 2 pbw to about 20 pbw of a surfactant system comprising at least:
   a) one lauramphoacetate, and
   b) one sulfosuccinate.

Surprisingly it has been found that the surfactant mixture used in the compositions according to the invention makes it possible to achieve an acceptable compromise between the following attributes: viscosity of the composition, foaming properties and conditioning on target area, at an equivalent or even decreased overall amount of surfactant and at a reasonable cost.

The presence of a synergic surfactant mixture in the compositions according to the invention was demonstrated by foam measurements and sensorial tests using an expert panel.

It has also been found that the specific cationic guar used in the compositions according to the invention makes it possible to increase oil deposition on target area, i.e. the amount of oil deposited on target area is significantly higher compared to compositions containing alternative cationic guars. This increased oil deposition results in improved conditioning.

Improved conditioning can allow avoiding the use of large quantities of composition. It can also allow lowering the frequency of the use of the composition. It can also allow avoiding build-up deposition, especially on virgin hair where not much treatment is needed.

The present invention is also directed toward the use of a composition of the invention for washing keratin substrates, in particular the hair or the scalp.

By the expression "sulfate-containing surfactants free composition" or "sulfate-free composition" it is meant that the composition of the invention is devoid of, i.e. does not contain (0%) any anionic surfactant which is a derivative of a sulfate, such as especially sodium lauryl sulfate (SLS), sodium laureth sulfate (SLES), ammonium lauryl sulfate (ALS) or ammonium laureth sulfate (ALES).

For the purposes of the present invention, the term "anionic surfactant which is a derivative of a sulfate" means surfactants comprising at least one anionic group or group that can be ionized into an anionic group, chosen from sulfate functions (—$OSO_3H$ or —$OSO_3$—).

Thus, the following anionic surfactants are preferably not present in the composition according to the invention: salts of alkyl sulfates, of alkylamide sulfates, of alkyl ether sulfates, of alkylamido ether sulfates, of alkylaryl ether sulfates, of monoglyceride sulfates.

By the expression "composition having a satisfactory viscosity" it is meant here a composition that has an apparent viscosity comprised between 1,500 and 50,000 cps, for instance comprised between 2,000 and 30,000 cps, for instance comprised between 3,000 and 25,000 cps. The apparent viscosity of each composition was measured after 24-hours in a temperature-controlled room (21±3° C.), using a Brookfield Viscosimeter Model DV-II+ at 10 RPM, with a RV spindle 4 or 5. The viscosity value was always taken after a stabilization time of 1 min.

According to one embodiment, the composition of the invention has an apparent viscosity of at least 1,500 cps, for instance of at least 2,000 cps.

According to anyone of the invention embodiments, the composition of the invention has an apparent viscosity lower than 50,000 cps, for instance lower than 40,000 cps.

By the expression "foaming properties" it is meant especially here flash foam and foam volume, which are among the main factors affecting the consumer perception about the foam quality. Well-known tests, notably as described in the experimental part, may be used to measure these factors.

By the expression "conditioning on target area" it is meant imparting positive properties to the target area. The target area may be especially a keratinous substrate. As used herein, "keratinous substrates" include, but are not limited to, skin, hair, scalp, lips, eyelashes and nail. Preferably the target area is skin, hair and/or scalp.

For example in the case where the target area is hair "improved conditioning" may cover improved ease of detangling and/or ease of combing.

Ease of detangling may be determined by the measurement of the time required for detangling the hair. The shorter the detangling time is, the easier the hair to detangle is.

Ease of combing may be determined by the measurement of the work required for combing the hair. The lower the combing work is, the easier the hair to comb is.

In the case where the target area is skin, "improved conditioning" may cover improved moisturizing benefits and/or softness.

Conditioning may also be determined by the measurement of the amount of oil deposited on target area. The higher the amount of oil deposited on target area, the higher the resulting conditioning.

Advantageously the compositions of the invention are mild compositions.

Mildness may be assessed for instance with the Zein test, which is a conventional method for analyzing the dermal irritation potential of a product.

The terms "consists of or"consisting of in relation to the surfactant system of the composition of the invention are used here to meant that the composition of the invention comprises a surfactant system which is strictly formed of a mixture of the surfactants that are expressly recited, and contains no other surfactants.

The composition of the invention is a personal care composition, preferably a personal care cleansing composition, that is to say a composition aimed to the washing/cleaning and in particular for a body-care application, such as but not limited to a shower gel, a facial cleanser, a body-wash, a liquid hand soap, a shampoo or a cleansing conditioner.

All amounts are in parts by weight (pbw) relative to the total weight of the composition.

For the avoidance of any doubt the amounts of surfactant refer to the actual amount of active surfactant compound present in the composition. In other words, it does not include the residue which may be present as an impurity in a commercially available surfactant mixture.

Should the disclosure of any patents, patent applications, and publications which are incorporated herein by reference conflict with the description of the present application to the extent that it may render a term unclear, the present description shall take precedence.

The composition of the present invention comprises from about 0.2 pbw to about 15 pbw of a derivatized cationic guar comprising cationic substituent groups and non ionic substituent groups.

Derivatized guars are polymers obtained by chemically modifying guar gum. The chemical modification is often referred to as derivatization. The modification provides side groups on the guar polymer backbone. The side groups are usually linked to the backbone by ether linkage. The oxygen of the ether linkage corresponds to hydroxyl groups on the guar backbone, reacted for modification. Guar comes from guar gum, the mucilage found in the seed of the leguminous plant Cyamopsis tetragonolobus. The guar seeds used to make guar gum are composed of a pair of tough, non-brittle endosperm sections, hereafter referred to as "guar splits," between which is sandwiched the brittle embryo (germ). After dehulling, the seeds are split, the germ (43-47% of the seed) is removed by screening. The splits typically contain about 78-82% guar gum and minor amounts of some proteinaceous material, inorganic salts, water-insoluble gum, and cell membranes, as well as some residual seed coat and seed embryo.

The water soluble fraction (85%) is called "guaran" or "guar gum" which consists of linear chains of (1,4)-. β-D mannopyranosyl units-with α-D-galactopyranosyl units attached by (1,6) linkages. The ratio of D-galactose to D-mannose is about 1:2. The backbone of guar is herein understood as comprising the mannose and the galactose groups.

Modifications by a cationic substituent group are known by the one skilled in the art.

According to any one of the invention embodiments, the cationic substituent group in the derivatized cationic guar of the invention comprises a cationic nitrogen radical, more typically a quaternary ammonium radical.

Typical quaternary ammonium radicals are trialkylammonium radicals, such as trimethylammonium radicals, triethylammonium radicals, tributylammonium radicals, aryldialkylammonium radicals, such as benzyldimethylammonium radicals, and ammonium radicals in which the nitrogen atom is a member of a ring structure, such as pyridinium radicals and imidazoline radicals, each in combination with a counterion, typically a chloride, bromide, or iodide counterion.

According to any one of the invention embodiments, the cationic substituent group is linked to the reactive functional group of the cationizing agent, for example, by an alkylene or oxyalkylene linking group. Suitable cationizing reagents include, for example, epoxy-functional cationic nitrogen compounds, such as, for example, 2,3-epoxypropyltrimethylammonium chloride; chlorohydrin-functional cationic nitrogen compounds, such as, for example, 3-chloro-2-hydroxypropyl trimethylammonium chloride, 3-chloro-2-hydroxypropyl-lauryldimethylammonium chloride, 3-chloro-2-hydroxypropyl-stearyldimethylammonium chloride; and vinyl-, or (meth)acrylamide-functional nitrogen compounds, such as methacrylamidopropyl trimethylammonium chloride.

According to any one of the invention embodiments the cationic substituent group may be for example hydroxypropyl ammonium. These can be obtained for example by reacting guar gum with compounds such as 2,3-epoxypropyltrimethylammonium chloride or 3-chloro-2-hydroxypropyltrimethylammonium chloride. Guars bearing only such cationic substituent groups are referred to, according to INCI terminology, as Guar Hydroxypropyltrimonium Chloride. Jaguar C14S provided by Rhodia is a typical example of Guar Hydroxypropyltrimonium Chloride.

Modifications by a non ionic substituent group are known by the one skilled in the art.

According to any one of the invention embodiments, the non ionic substituent group in the derivatized cationic guar of the invention comprises a hydroxyalkyl and/or poly (alkyleneoxy) radical.

Hydroxyalkyl and/or poly(alkyleneoxy) radicals can be typically added to the guar polysaccharide chains by reacting the guar with an alkylene oxide derivatizing agent, such as ethylene oxide, propylene oxide, or butylene oxide, under known alkoxylation conditions According to any one of the invention embodiments, the non ionic substituent group in the derivatized cationic guar of the invention comprises a hydroxypropyl radical.

A hydroxypropyl radical can be typically added to the guar polysaccharide chains by reacting the guar with reactants such as propylene oxide.

Derivatized cationic guar comprising cationic substituent groups and non ionic substituent groups are known by the one skilled in the art. Some are referred to, according to INCI terminology, as Hydroxypropyl Guar Hydroxypropyltrimonium Chloride.

According to any one of the invention embodiments, the derivatized cationic guar of the invention is a Hydroxypropyl Guar Hydroxypropyltrimonium Chloride.

Jaguar C162 provided by Rhodia is a typical example of Hydroxypropyl Guar Hydroxypropyltrimonium Chloride.

Jaguar LS, which is also a Hydroxypropyl Guar Hydroxypropyltrimonium Chloride provided by Rhodia, is particularly suitable as derivatized cationic guar of the invention.

According to any one of the invention embodiments, the degree of modification by the non ionic substituent group (molar substitution or MS) is preferably between 0.1 and 1.2, preferably of between 0.3 and 0.7.

According to any one of the invention embodiments, the degree of modification by the cationic substituent group (degree of substitution or DS) is preferably between 0.01 and 0.6, preferably between 0.05 and 0.20.

According to any one of the invention embodiments, the derivatized cationic guar of the invention has a weight-average molar mass of at least 10,000 g/mol, and more preferably of higher than 100,000 g/mol, preferably of higher than 500,000 g/mol, for example of from 500,000 g/mol to 3,000,000 g/mol, for example of from 500,000 to 1,500,000 g/mol or even more, depending on their possible degree of polymerization.

The composition of the present invention comprises at least 0.05 pbw of an oil.

The oil may be for example a silicone oil, an oil of mineral origin, an oil of vegetable origin, or a mixture or association thereof.

The oil is typically present in the composition in the form of dispersed particles or droplets.

According to any one of the invention embodiments, the composition of the present invention comprises from 0.05 to 10 pbw, for example from 0.1 to 5 pbw of the oil.

According to any one of the invention embodiments, the composition comprises a silicone oil. Silicone oils are known by the one skilled in the art. These are often referred to as polyorganosiloxanes. In the present application the terms “silicone” or “polyorganosiloxane” can be used indifferently. The term “silicone” or “polyorganosiloxane” is understood to mean any organosiloxane compound comprising alkyl (for example methyl) groups and/or functionalized by groups other than alkyl groups. Silicones can be linear, cyclic, or branched polymers or oligomers of monomeric silicon/oxygen (organosiloxane) monomers, optionally bearing some further functional groups. The polymeric backbone is typically made up of alternating silicon and oxygen atoms. The silicon atoms may carry a wide variety of substituents which can be the same or different. Functional end-blocking groups may carry nitrogen or hydroxyl moieties.

The polyorganosiloxane is advantageously (in shampoos and conditioners in particular) a nonvolatile and water-insoluble polyorganosiloxane. It advantageously exhibits a viscosity of between 1000 and 2 000 000 mPa·s, preferably between 5000 and 500 000 mPa·s. The polyorganosiloxane can in particular be a polydimethylorganosiloxane (“PDMS”, INCI name: dimethicone), or a polyorganosiloxane exhibiting amine groups (for example, amodimethicone according to the INCI name), quaternary ammonium groups (for example, silicone quaternium −1 to −10 according to the INCI name), hydroxyl groups (terminal or non terminal), polyoxyalkylene groups, for example polyethylene oxide and/or polypropylene oxide groups (as terminal groups, as blocks within a PDMS chain or as grafts), or several of these groups.

According to any one of the invention embodiments the amount of silicone oil present in the composition can typically be from 0.1 to 5 pbw, for example from 0.5 to 2 pbw.

The silicone oil (polyorganosiloxane) is preferably present in the composition in an emulsion form (liquid silicone droplets dispersed in the aqueous phase). The silicone oil can be present in the composition in the form of:

- a microemulsion with a particle size of lower than 0.15 μm,
- an emulsion with a particle size of from 0.15 μm to lower than 1 μm, or of from 1 μm to lower than 1.5 μm or of from 1.5 μm to lower than 2 μm, or from 2 μm to lower than 2.5 μm, or from 2.5 μm to lower than 4 μm, or from 4 μm to lower than 10 μm, or from 10 μm to lower than 30 μm, or from 30 μm to 100 μm. Sizes herein refer to mean sizes of the droplets.

The droplets of the emulsion can be more or less large in size. Reference may thus be made to microemulsions, to miniemulsions or to macroemulsions. In the present patent application, the term "emulsion" covers in particular all these types of emulsion. Without wishing to be committed to any one theory, it is specified that microemulsions are generally thermodynamically stable systems generally comprising large amounts of emulsifying agents. The other emulsions are generally systems in the non-thermodynamically stable state which retain for a certain time, in the metastable state, the mechanical energy provided during the emulsification. These systems generally comprise lesser amounts of emulsifying agents.

The emulsions can be obtained by mixing the carrier, preferably aqueous carrier, the polyorganosiloxane and generally an emulsifying agent, and then emulsifying. It is possible to speak of in situ emulsification.

The compositions in the emulsion form can also be obtained by mixing the carrier, preferably aqueous carrier, with a pre-prepared emulsion of droplets comprising the polyorganosiloxane in an external phase which is preferably miscible with the cosmetically acceptable carrier, preferably of the same nature as said carrier, preferably an aqueous carrier. This embodiment may be preferred as it is simple to implement. In addition, this embodiment is particularly suitable for the implementation of cosmetic compositions in which the polyorganosiloxane is in the microemulsion form. It is possible to speak of pre-emulsification.

According to a specific embodiment, the emulsion is a microemulsion, the size of the droplets of which is less than 0.15 μm. In this embodiment, the composition preferably comprises a proportion of emulsifying agent of greater than 10 pbw, preferably at least 15 pbw, with respect to the weight of According to an advantageous form, the microemulsion is transparent. The microemulsion can, for example, exhibit a transmittance of at least 90%, preferably of at least 95%, at a wavelength of 600 nm, measured, for example, using a Lambda 40 UV-Vis spectrometer at a concentration of 0.5% by weight in water. In this context, the cosmetic composition can advantageously be transparent. It can, for example, exhibit a transmittance of at least 90%, preferably of at least 95%, at a wavelength of 600 nm, measured, for example, using a Lambda 40 UV-Vis spectrometer. polyorganosiloxane. The size of the microemulsion droplets can be measured on an emulsion prepared prior to this introduction into the cosmetic composition by dynamic light scattering (QELS), for example as described below. The equipment used is, for example, composed of a Spectra-Physics 2020 laser, of a Brookhaven 2030 correlator and of the associated computing. As the sample is concentrated, it is diluted in deionized water and filtered through a 0.22 μm filter in order, at the end, to be at 2% by weight. The diameter obtained is an apparent diameter. The measurements are carried out at angles of 90° and 135°. For the size measurements, in addition to the conventional analysis by cumulants, the autocorrelation function is run in three ways (the exponential sampling or EXPSAM described by Pr. Pike, the "Non Negatively Constrained Least Squares" or NNLS method and the CONTIN method described by Pr. Provencher) which each give a size distribution weighted by the scattered intensity and not by the weight or the number. The refractive index and the viscosity of the water are taken into account.

According to another specific embodiment, the emulsion is an emulsion for which the mean size of the droplets is greater than or equal to 0.15 μm, for example greater than 0.5 μm, or than 1 μm, or than 2 μm, or than 10 μm, or than 20 μm, and preferably less than 100 μm. The size of the droplets can be measured, by optical microscopy and/or laser particle sizing (Horiba LA-910 laser scattering analyzer), on an emulsion prepared prior to its introduction into the cosmetic composition or directly on the cosmetic composition diluted in water. In this embodiment, the composition preferably comprises a proportion of emulsifying agent of less than 10% by weight, with respect to the weight of polyorganosiloxane.

Emulsifying agents of use in the preparation of polyorganosiloxane emulsions are in particular nonionic surfactants, preferably polyalkoxylated surfactants, for example chosen from alkoxylated fatty alcohols, alkoxylated triglycerides, alkoxy lated fatty alcohols, alkoxylated sorbitan esters, alkoxylated fatty amines, alkoxylated di(1-phenylethyl) phenols, alkoxylated tri (1-phenylethyl)phenols and alkoxylated alkylphenols, where the number of alkoxy units, more particularly oxyethylene and/or oxypropylene units, is such that the HLB value is greater than or equal to 10.

Mention may be made, among the silicone derivatives which are soluble in the water of the composition, inter alia, of dimethicone copolyols.

As relates to the silicones which are provided in the form of dispersions which are insoluble in the water of the composition, use may suitably be made of water-insoluble and nonvolatile polyorganosiloxanes, among which may be mentioned polyalkylsiloxane, polyarylsiloxane or polyalkylarylsiloxane oils, gums or resins or their water-insoluble functionalized derivatives, or their mixtures, which are nonvolatile.

Said organopolyosiloxanes are regarded as water-insoluble and nonvolatile if their solubility in water is less than 50 g/liter and their intrinsic viscosity is at least 3000 mPa·s at 25° C.

Mention may be made, as examples of water-insoluble and nonvolatile polyorganosiloxanes or silicones, of silicone gums, such as, for example, a diphenyl dimethicone gum, and preferably the polydimethylsiloxanes exhibiting a viscosity at least equal to 6×105 mPa·s at 25° C. and more preferably still those with a viscosity of greater than 2×106 mPa·s at 25° C.

According to the invention, the water-insoluble and nonvolatile polyorganosiloxane or silicone occurs in a form dispersed within the cosmetic composition including it.

The water-insoluble and nonvolatile polyorganosiloxane or silicone exists in the form of particles or droplets, the size of which can be chosen according to the nature of the cosmetic composition or the performance desired for said composition. Generally, this size can vary from 0.01 to 70 microns.

In order to facilitate the use thereof, these polyorganosiloxanes can be dispersed or dissolved beforehand in volatile or nonvolatile silicone derivatives of low viscosity and then emulsified in the cosmetic composition.

Mention may be made, among these silicones of low viscosity, of volatile cyclic silicones and polydimethylsiloxanes of low weight.

Use can also be made of functionalized silicone derivatives, such as aminated derivatives, directly in the form of emulsions or starting from a preformed microemulsion. They can be compounds known under the term of aminated silicones or hydroxylated silicones.

Mention is in particular made, as polyorganosiloxanes which can be used, of:

- polyorganosiloxanes comprising —Si(CH3)2O— units and —SiY(CH3)O— units where Y is a —(CH2)3—NH(CH2)2—NH2 or —(CH2)3—NH2 group,

- polyorganosiloxanes comprising —Si(CH3)2O— units and HO—Si(CH3)2O— terminal units and/or —Si(CH3)(OH)O— nonterminal units,
- polyorganosiloxanes comprising —Si(CH3)2O— units and —SiY(CH3)O— units where Y is —LX-Zx-Palc where LX is a divalent connecting group, preferably an alkylene group, ZX is a covalent bond or a divalent joining group comprising a heteroatom, Palc is a group of formula [OE]s-[OP]1-X', in which OE is a group of formula —CH2—CH2—O—, OP is a group of formula —CH2—CHCH3—O— or —CHCH3—CH2—O—, X' is a hydrogen atom or a hydrocarbon group, s is a mean number greater than 1 and t is a mean number greater than or equal to 0,
- polyorganosiloxanes, the chain of which comprises at least one block comprising units of formula —Si(CH3)2O— units and at least one-[OE]s-[OP]t-block,
- polyorganosiloxanes comprising —Si(CH3)2O— units and/or —Si(CH3)RO— and/or —SiR2O— and/or R—Si(CH3)2O— and/or H3C—SiR2O— and/or R—SiR2O— units, where R, which can be identical or different, is an alkyl group other than a methyl group, an aryl group, an alkylaryl group or an aralkyl group.

Examples of silicone oils that can be used include the following (INCI names):

Amino Bispropyl Dimethicone; Aminopropyl Dimethicone; Aminopropyl Phenyl Trimethicone; Amodimethicone; Amodimethicone Hydroxystearate; Amodimethicone/Silsesquioxane Copolymer; Behentrimonium Dimethicone PEG-8 Phthalate; Bisamino PEG/PPG-41/3 Aminoethyl PG-Propyl Dimethicone; Bis-Aminopropyl Dimethicone; Bis-Aminopropyl/Ethoxy Aminopropyl Dimethicone; Bis-Butyldimethicone Polyglyceryl-3; Bis-Butyloxyamodimethicone/PEG-60 Copolymer; Bis(C13-15 Alkoxy) Hydroxybutamidoamodimethicone; Bis(C13-15 Alkoxy) PG-Amodimethicone; Bis-Hydroxyethoxypropyl Dimethicone Beeswax Esters; Bis-Hydroxyethoxypropyl Dimethicone Isostearate; Bis-Isobutyl PEG-14/Amodimethicone Copolymer; Bis-Isobutyl PEG-15/Amodimethicone Copolymer; Bis-PEG-1 Dimethicone; Bis-PEG-4 Dimethicone; Bis-PEG-8 Dimethicone; Bis-PEG-12 Dimethicone; Bis-PEG-20 Dimethicone; Bis-PEG-12 Dimethicone Beeswax; Bis-PEG-12 Dimethicone Candelillate; Bis-PEG-10 Dimethicone/Dimer Dilinoleate Copolymer; Bis-PEG-15 Methyl Ether Dimethicone; Bisphenylhexamethicone; Bis-Phenylpropyl Dimethicone; Bis-(Polyglyceryl-3 Oxyphenylpropyl) Dimethicone; Bis(PPG-7 Undeceneth-21) Dimethicone; Borage Seed Oil PEG-7 Dimethicone Esters; C30-45 Alkyl Cetearyl Dimethicone Crosspolymer; C26-28 Alkyl Dimethicone; Cetearyl Dimethicone/Vinyl Dimethicone Crosspolymer; Cetrimonium Carboxydecyl PEG-8 Dimethicone; Cetyl Triethylmonium Dimethicone PEG-8 Phthalate; Cetyl Tricthylmonium Dimethicone PEG-8 Succinate; Cyclohexasiloxane; Cyclomethicone; Cyclopentasiloxane; Cyclophenylmethicone; Cyclotetrasiloxane; Cyclotrisiloxane; DEA PG-Propyl PEG/PPG-18/21 Dimethicone; Dilinoleamidopropyl Dimethylamine, Dimethicone; Dimethicone PEG-7 Phosphate; Dimethicone Hydroxypropyl Trimonium Chloride; Dimethicone/Mercaptopropyl Methicone Copolymer; Dimethicone PEG-15 Acetate; Dimethicone PEG-8 Adipate; Dimethicone PEG-7 Avocadoate; Dimethicone PEG-8 Avocadoate; Dimethicone PEG-8 Beeswax; Dimethicone PEG-8 Borageate; Dimethicone PEG-7 Cocoate; Dimethicone PEG-7 Isostearate; Dimethicone PEG-7 Lactate; Dimethicone PEG-8 Lanolate; Dimethicone PEG-8 Meadowfoamate; Dimethicone PEG-7 Olivate; Dimethicone PEG-8 Olivate; Dimethicone PEG-8 Phosphate; Divinyldimethicone/Dimethicone Copolymer; Dimethicone PEG-7 Phthalate; Dimethicone PEG-8 Phthalate; Dimethicone PEG-7 Succinate; Dimethicone PEG-8 Succinate; Dimethicone PEG-7 Sulfate; Dimethicone PEG-7 Undecylenate; Dimethicone Propyl PG-Betaine; Dimethicone/Silsesquioxane Copolymer; Dimethiconol Arginine; Dimethiconol Cysteine; Dimethiconol Lactate; Dimethiconol Methionine; Dimethiconol Panthenol; Dimethiconol/Silsesquioxane Copolymer; Di-Methoxycinnamidopropyl Ethyldimonium Chloride Ether; Dimethoxysilyl Ethylenediaminopropyl Dimethicone; Dimethylaminopropylamido PCA Dimethicone; Diphenyl Amodimethicone; Diphenylisopropyl Dimethicone; Diphenylsiloxy Phenyl Trimethicone; Glycidoxy Dimethicone; Hexyl Dimethicone; Hydrolyzed Collagen PG-Propyl Dimethiconol; Hydrolyzed Collagen PG-Propyl Methylsilanediol; Hydrolyzed Collagen PG-Propyl Silanetriol; Hydrolyzed Keratin PG-Propyl Methylsilanediol; Hydrolyzed Sesame Protein PG-Propyl Methylsilanediol; Hydrolyzed Silk PG-Propyl Methylsilanediol; Hydrolyzed Silk PG-Propyl Methylsilanediol Crosspolymer; Hydrolyzed Soy Protein/Dimethicone PEG-7 Acetate; Hydrolyzed Soy Protein PG-Propyl Methylsilanediol; Hydrolyzed Vegetable Protein PG-Propyl Silanetriol; Hydrolyzed Wheat Protein/Cystine Bis-PG-Propyl Silanetriol Copolymer; Hydrolyzed Wheat Protein PG-Propyl Methylsilanediol; Hydrolyzed Wheat Protein PG-Propyl Silanetriol; Hydroxypropyldimethicone; Isopolyglyceryl-3 Dimethicone; Isopolyglyceryl-3 Dimethiconol; Lauryl PEG-9 Polydimethylsiloxyethyl Dimethicone; Lauryl Polyglyceryl-3 Polydimethylsiloxyethyl Dimethicone; Linoleamidopropyl PG-Dimonium Chloride Phosphate Dimethicone; Methoxy Amodimethicone/Silsesquioxane Copolymer; Methyleugenyl PEG-8 Dimethicone; Methylsilanol Acetylmethionate; Methylsilanol Elastinate; Methyl Trimethicone; Nylon-611/Dimethicone Copolymer; PCA Dimethicone; PEG-8 Amodimethicone; PEG-3 Dimethicone; PEG-8 Dimethicone; PEG-9 Dimethicone; PEG-10 Dimethicone; PEG-12 Dimethicone; PEG-14 Dimethicone; PEG-17 Dimethicone; PEG-8 Distearmonium Chloride PG-Dimethicone; PEG-8 Methicone; PEG-6 Methicone Acetate; PEG-6 Methyl Ether Dimethicone; PEG-7 Methyl Ether Dimethicone; PEG-8 Methyl Ether Dimethicone; PEG-9 Methyl Ether Dimethicone; PEG-10 Methyl Ether Dimethicone; PEG-11 Methyl Ether Dimethicone; PEG-32 Methyl Ether Dimethicone; PEG-10 Nonafluorohexyl Dimethicone Copolymer; PEG-12 Methyl Ether Lauroxy PEG-5 Amidopropyl Dimethicone; PEG-8 PG-Coco-Glucoside Dimethicone; PEG/PPG-28/21 Acetate Dimethicone; PEG/PPG-20/22 Butyl Ether Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-27/9 Butyl Ether Dimethicone; PEG/PPG-10/2 Dimethicone; PEG/PPG-20/23 Dimethicone; PEG/PPG-20/22 Methyl Ether Dimethicone; PEG/PPG-24/24 Methyl Ether Glycidoxy Dimethicone; PEG/PPG-10/3 Oleyl Ether Dimethicone; PEG-4 Trifluoropropyl Dimethicone Copolymer; PEG-8 Trifluoropropyl Dimethicone Copolymer; PEG-10 Trifluoropropyl Dimethicone Copolymer; PG-Amodimethicone; Phenyl Methiconol; Phenylpropyldimethylsiloxysilicate; Phenylpropyl Ethyl Methicone; Phenyl Propyl Trimethicone; Phenyl Trimethicone; Polydimethylsiloxy PPG-13 Butyl Ether Silsesquioxane; Polyglyceryl-3 Disiloxane Dimethicone; Polyglyceryl-3 Polydimethylsiloxyethyl Dimethicone; Polysilicone-1; Polysilicone-2; Polysilicone-3; Polysilicone-4; Polysilicone-5; Polysilicone-6; Polysilicone-7; Polysilicone-8; Polysilicone-10; Polysilicone-13; Polysilicone-14; Polysilicone-18; Polysilicone-18 Cetyl Phosphate; Polysilicone-18 Stearate; PPG-12 Butyl Ether Dimethicone; PPG-12 Dimethicone; PPG-27 Dimethicone; Propoxytetramethyl Piperidinyl Dimethicone; Quaternium-80; Silicone Quaternium-1; Silicone Quaternium-2; Silicone Quaternium-2 Panthenol Succinate; Silicone Quaternium-3; Silicone Quaternium-4; Silicone Quaternium-5; Silicone Quaternium-6; Silicone Quaternium-7; Silicone Quaternium-8; Silicone Quaternium-9; Silicone Quaternium-10; Silicone Quaternium-11; Silicone Quaternium-12; Silicone Quaternium-15; Silicone Quaternium-16; Silicone Quaternium-16/Glycidoxy Dimethicone Crosspolymer; Silicone Quaternium-17; Silicone Quaternium-18; Silicone Quaternium-20; Sodium Dimethicone PEG-7 Acetyl Methyltaurate; Stearalkonium Dimethicone PEG-8 Phthalate; Steardimonium Hydroxypropyl Panthenyl PEG-7 Dimethicone Phosphate Chloride; Steardimonium Hydroxypropyl PEG-7 Dimethicone Phosphate Chloride; Trideceth-9 PG-Amodimethicone; Trifluoropropyl Cyclopentasiloxane; Trifluoropropyl Cyclotetrasiloxane; Trifluoropropyl Dimethicone; Trimethylsiloxyamodimethicone; Trimethylsiloxyphenyl Dimethicone; Gluconamidopropyl Aminopropyl Dimethicone; Cetrimonium Dimethicone PEG-7 Phthalate; Stearyl Aminopropyl Methicone; Myristylamidopropyl Dimethylamine Dimethicone PEG-7 Phosphate; Potassium Dimethicone PEG-7 Panthenyl Phosphate; Sodium PG-Propyldimethicone Thiosulfate Copolymer; Sodium PG-Propyl Thiosulfate Dimethicone; Tetrabutoxypropyl Trisiloxane.

According to any one of the invention embodiments, the composition of the present invention comprises a silicone oil selected from the group consisting of a dimethicone, an amodimethicone, a dimethiconol, a PEG-dimethicone, or a mixture or association thereof.

According to any one of the invention embodiments, the composition comprises an oil of mineral origin. Such compounds are known by the one skilled in the art.

Typical examples of oils of mineral origin that can be used include the following (INCI names): Petrolatum, Mineral Oil, Hydrogenated Polydodecene, Hydrogenated Polydecene, and Polydecene.

According to any one of the invention embodiments, the composition comprises an oil of vegetable origin. Such compounds are known by the one skilled in the art.

Typical examples of oils of vegetable origin that can be used include the following (INCI names):

Adansonia Digitata Seed Oil; Alpinia Speciosa Leaf Oil; Argemone Mexicana Oil; Brassica Oleracea Italica (Broccoli) Seed Oil; Calodendrum Capense Nut Oil; Calophyllum Inophyllum Seed Oil; Camellia Chekiangoleosa Seed Oil; Carica Papaya Seed Oil; Cedrus Deodara Seed Oil; Cocos Nucifera (Coconut) Oil; Crambe Abyssinica Seed Oil; Egg Oil; Fragaria Ananassa (Strawberry) Seed Oil; Hydrogenated Camellia Oleifera Seed Oil; Hydrogenated Evening Primrose Oil; Hydrogenated Hazelnut Oil; Hydrogenated Lanolin; Hydrogenated Macadamia Seed Oil; Hydrogenated Rice Bran Oil; Hydrogenated Sesame Seed Oil; Hydroxylated Jojoba Oil; Isobutylated Lanolin Oil Lanolin Oil; Lesquerella Fendleri Seed Oil; Marmot Oil; Mink Oil; Ocimum Tenuiflorum Oil; Orbignya Cohune Seed Oil; Ostrich Oil; Phormium Tenax Seed Oil; PPG-40-PEG-60 Lanolin Oil; PPG-12-PEG-65 Lanolin Oil; Pongamia Glabra Seed Oil; Pinus Parviflora Seed Oil; Sclerocarya Birrea Seed Oil; Schleichera Trijuga Seed Oil; Simmondsia Chinensis (Jojoba) Seed Oil; Sorbus Aucuparia Seed Oil; Zea Mays (Corn) Oil; Bertholletia Excelsa Seed Oil PEG-8 Esters; Coconut Oil Methylpropanediol Esters; Jojoba Oil PEG-8 Esters; Hydrogenated Castor Oil Behenyl Esters; Hydrogenated Castor Oil Cetyl Esters; Hydrogenated Castor Oil Dimer Dilinoleate; Hydrogenated Castor Oil Stearyl Esters; Hydrogenated Olive Oil Caprylyl Esters; Hydrogenated Olive Oil Cetyl Esters; Hydrogenated Olive Oil Decyl Esters; Hydrogenated Olive Oil Hexyl Esters; Hydrogenated Olive Oil Lauryl Esters; Hydrogenated Olive Oil Myristyl Esters; Hydrogenated Olive Oil Stearyl Esters; Orbignya Oleifera Seed Oil PEG-8 Esters; Passiflora Edulis/Passiflora Incarnata Seed Oils PEG-8 Esters; Brassica Campestris (Rapeseed) Oil Unsaponifiables; Brassica Oleracea Botrytis (Cauliflower) Oil Unsaponifiables; Butyrospermum Parkii (Shea Butter) Unsaponifiables; Canola Oil Unsaponifiables; Citrus Aurantifolia (Lime) Seed Oil Unsaponifiables; Citrus Aurantium Dulcis (Sweet Orange) Seed Oil Unsaponifiables; Citrus Grandis (Grapefruit) Seed Oil Unsaponifiables; Hydrogenated Apricot Oil Unsaponifiables; Hydrogenated Grapefruit Seed Oil Unsaponifiables; Hydrogenated Lime Seed Oil Unsaponifiables; Hydrogenated Olive Oil Unsaponifiables; Hydrogenated Orange Seed Oil Unsaponifiables; Hydrogenated Sweet Almond Oil Unsaponifiables; Hydrogenated Wheat Germ Oil Unsaponifiables Helianthus Annuus (Sunflower) Seed Oil Unsaponifiables; Lupinus Albus Oil Unsaponifiables; Medicago Sativa (Alfalfa) Oil Unsaponifiables; Olea Europaea (Olive) Oil Unsaponifiables; Olea Europaea (Olive) Fruit Unsaponifiables; Persea Gratissima (Avocado) Oil Unsaponifiables; Prunus Armeniaca (Apricot) Kernel Oil Unsaponifiables S; esamum Indicum (Sesame) Oil Unsaponifiables; Triticum Vulgare (Wheat) Germ Oil Unsaponifiables; Zea Mays (Corn) Oil Unsaponifiables.

The composition of the invention also comprises from about 2 pbw to about 20 pbw of a surfactant system comprising at least one lauramphoacetate, and one sulfosuccinate. According to any one of the invention embodiments, the sulfosuccinate may be a monoalkyl sulfosuccinate of formula $R^cO_2CCH_2CH(SO_3X^c)CO_2X^c$, an amido-MEA sulfosuccinate of formula $R^cCONHCH_2CH_2O_2CCH_2CH(SO_3X^c)CO_2X^c$, an amido-MIPA sulfosuccinate of formula $R^cCONH(CH_2)CH(CH_3)(SO_3X^c)CO_2X^c$ or an alkoxylated sulfosuccinate of formula $R^c—O—(CH_2CH_2O)_nC(O)CH_2CH(SO_3X^c)CO_2X^c$, wherein n ranges from 1 to 20, $R^c$ is a substituted or unsubstituted alkyl, alkenyl, aryl or alkylaryl group having 6 to 30 carbon atoms, and $X^c$ is a counterion.

According to any one of the invention embodiments, the sulfosuccinate may be an alkoxylated sulfosuccinate of formula $R^c—O—(CH_2CH_2O)_nC(O)CH_2CH(SO_3X^c)CO_2X^c$, wherein n ranges from 2 to 20, $R^c$ is an unsubstituted alkyl group having 6 to 30 carbon atoms, for instance 7 to 24 carbon atoms, for instance 7 to 21 carbon atoms, and $X^c$ is a counterion.

The counterion $X^c$ of the sulfosuccinate may be an alkali metal ion, alkaline earth metal ion or ammonium ion.

The counterion $X^c$ of the sulfosuccinate is typically an alkali metal ion, in particular a sodium ion or an ammonium ion, in particular $NH_4^+$. It may alternatively be another alkali metal ion, such as potassium or lithium, an alkaline earth metal ion, such as calcium and magnesium, or an optionally substituted ammonium ion, such as an alkyl ammonium having up to 6 aliphatic carbon atoms including isopropylammonium, monoethanolammonium, diethanolammonium and triethanolammonium.

According to any one of the invention embodiments, the sulfosuccinate is an alkoxylated sulfosuccinate selected from ammonium and sodium lauryl ether sulfosuccinates.

According to anyone of the invention embodiments, said sulfosuccinate is present in a concentration ranging from 0.1 to 10 pbw relative to the total weight of the composition, for example from 1 to 8 pbw, for example from 2 to 6 pbw According to any one of the invention embodiments, the surfactant system may comprise as optional component additional sulfate-free surfactants, which can be selected amongst anionic surfactant different from sulfosuccinate, amphoteric or zwitterionic surfactants different from lauramphoacetate or non ionic surfactants.

According to any one of the invention embodiments, the composition of the present invention may further comprise at least one taurate, for instance one methyl alkyl taurate of formula $R^aCON(CH_3)CH_2CH_2SO_3X^a$, in which $R^a$ is a linear or branched alkyl group or alkenyl group having 6 to 30, for instance 8 to 22 carbon atoms and $X^a$ is a counterion.

The counterion $X^a$ may be an alkali metal ion, alkaline earth metal ion or ammonium ion.

The counterion $X^a$ is typically an alkali metal ion, in particular a sodium ion. It may alternatively be another alkali metal ion, such as potassium or lithium, an alkaline earth metal ion, such as calcium and magnesium, or an optionally substituted ammonium ion, such as an alkyl ammonium having up to 6 aliphatic carbon atoms including isopropylammonium, monoethanolammonium, diethanolammonium and triethanolammonium.

Typical examples of taurates are methyl cocoyl taurate and methyl oleoyl taurate.

According to anyone of the invention embodiments, the composition of the invention further comprises said methyl alkyl taurate in a concentration ranging from 0.1 to 10 pbw relative to the total weight of the composition, for example from 0.5 to 5 pbw, for example from 1 to 3 pbw.

According to any one of the invention embodiments, the composition of the present invention may further comprise at least one isethionate of formula $R^bCOOCH_2CH_2SO_3\ X^b$, in which $R^b$ is a substituted or unsubstituted alkyl, alkenyl, aryl or alkylaryl group having 6 to 30 carbon atoms, and $X^b$ is a counterion.

According to any one of the invention embodiments, the isethionate may be of formula $R^bCOOCH_2CH_2SO_3\ X^b$, with $R^b$ being an unsubstituted alkyl group having 6 to 30 carbon atoms, for instance 7 to 24 carbon atoms, for instance 7 to 21 carbon atoms.

In some embodiments, the component surfactant of the isethionate type may comprise a mixture of fatty acids to form a mixture of isethionates of formula $R^bCOOCH_2CH_2SO_3\ X^b$, in which $R^b$ may be different.

According to one embodiment, $R^b$ is a residue of a fatty acid.

Fatty acids obtained from natural oils often include mixtures of fatty acids. For example the fatty acid obtained from coconut oil contains a mixture of fatty acids including $C_{12}$ lauric acid, $C_{14}$ myristic acid, $C_{16}$ palmitic acid and $C_8$ caprylic acid.

$R^b$ may include the residue of one or more naturally occurring fatty acids and/or of one or more synthetic fatty acids.

Examples of carboxylic acids from which $R^b$ may be derived residue of include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, eruic acid, docosahexanoic acid, lignoceric acid, naturally occurring fatty acids such as those obtained from coconut oil, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof.

Most preferably $R^b$ comprises the residue of lauric acid, that is a saturated fatty acid having 12 carbon atoms, or the residue of mixed fatty acids derived from coconut oil.

The counterion $X^b$ of the isethionate may be an alkali metal ion, alkaline earth metal ion or ammonium ion.

The counterion $X^b$ of the isethionate is typically an alkali metal ion, in particular a sodium ion. It may alternatively be another alkali metal ion, such as potassium or lithium, an alkaline earth metal ion, such as calcium and magnesium, or an optionally substituted ammonium ion, such as an alkyl ammonium having up to 6 aliphatic carbon atoms including isopropylammonium, monoethanolammonium, diethanolammonium and triethanolammonium.

According to anyone of the invention embodiments, the composition of the invention further comprises said isethionate in a concentration ranging from 0.1 to 10 pbw relative to the total weight of the composition, for example from 0.5 to 5 pbw, for example from 1 to 3 pbw.

In one specific embodiment, the composition of the present invention may further comprise one or more nonionic surfactants selected from alkanolamide surfactants and glycoside surfactants.

Suitable alkanolamide surfactants are known compounds and include, for example, acetamide MEA, cocamide DEA, cocamide MEA, cocamide methyl MEA, cocamide MIPA, hydroxystearamide MEA, PEG-5 cocamide MEA, lactamide MEA, lauramide MEA and lauramide DEA, preferably cocamide MIPA or cocamide methyl MEA.

Suitable glycoside surfactants are known compounds and include, for example, $(C_4\text{-}C_{22})$alkylhexosides, such as butylglucoside, nonylglucoside, decylglucoside, dodecylglucoside, hexadecylglucoside, octadecylglucoside, cocoglucoside, laurylglucoside, caproyl ethyl glucoside, caprylyl/capryl glucoside, caprylyl glucoside, $(C_4\text{-}C_{22})$ alkylpolyhexosides, such as butylpolyglucosides, nonylpolyglucosides, decylpolyglucosides, tetradecylpolyglucosides, hexadecylpolyglucosides, erucylpolyglucosides, $(C_4\text{-}C_{22})$ alkylpentosides, such as nonylarabinosides, decylarabinoside, hexadecylarabinoside, octylxyloside, nonylxyloside, decylxyloside, hexadecylxyloside, erucylxyloside, and $(C_4\text{-}C_{22})$alkylpolypentosides, such as butylpolyarabinosides, nonylpolyarabinosides, decylpolyarabinosides, hexadecylpolyarabinosides, octadecylpolyarabinosides, erucylpolyarabinosides, butylpolyxylosides, nonylpolyxylosides, decylpolyxylosides, octadecylpolyxylosides, and erucylpolyxylosides, butylpoly(arabino-co-xylo)sides, nonylpoly(arabino-co-xylo)sides, decylpoly(arabino-co-xylo) sides, hexadecylpoly(arabino-co-xylo)sides, octadecylpoly (arabino-co-xylo)sides, erucylpoly(arabino-co-xylo)sides, and mixtures of any of such compounds, wherein the terminology "poly(arbino-co-xylo)side" denotes a copolymeric chain of monomeric residues of arabinose and xylose. Preferably the glycoside surfactant is decylglucoside.

According to a particular embodiment of the invention, said optional additional sulfate-free surfactants are incorporated in amounts varying between 0.5 and 5 pbw relative to the total weight of the composition.

According to any one of the invention embodiments, the composition of the invention further comprises of at least additional anionic surfactant different from sulfosuccinate chosen from taurate and isethionate and at least one nonionic surfactant chosen from alkanolamide surfactants and glycoside surfactants, and does not comprise any additional sulfate-free surfactants.

According to any one of the invention embodiments, the total amount of surfactants in a composition of the invention ranges from 5 to 15 pbw, relative to the total weight of the composition.

The weight ratio of anionic surfactants to amphoteric surfactants may typically range from 1:10 to 10:1.

According to any one of the invention embodiments, the composition of the invention may comprise an anionic-rich surfactant chassis, that is to say a surfactant chassis in which the ratio of anionic surfactants to amphoteric surfactants is greater than 1, for instance greater than 2.

In another embodiment of the invention, the composition of the invention may comprise an amphoteric-rich surfactant chassis, that is to say a surfactant chassis in which the ratio of amphoteric surfactants to anionic surfactants is greater than 1, for instance greater than 2.

According to any one of the invention embodiments, the composition of the present invention comprise, based on 100 pbw of such composition, from 0 to less than 2 pbw of one isethionate of formula (I'):

(I')

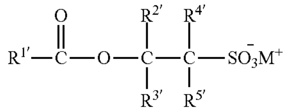

wherein $R^1$ represents a $C_{4-30}$ substituted or unsubstituted hydrocarbyl group; each of $R^{2'}$, and $R^{3'}$, $R^{4'}$ and $R^{5'}$ independently represents a hydrogen atom or a $C_{1-4}$ alkyl group and wherein at least one of $R^{2'}$, and $R^{3'}$, $R^{4'}$ and $R^{5'}$ is not hydrogen, and $M^+$ represents a cation.

Typical isethionates of formula (I') are sodium lauryl methyl isethionate and sodium cocoyl methyl isethionate.

Isethionates of formula (I') are not desirable components of the composition of the present invention.

More typically the composition of the present invention comprise, based on 100 pbw of such composition, from 0 to less than 1 pbw of isethionates of formula (I') and even substantially no isethionate of formula (I'), i.e. from 0 to less than 0.1 pbw isethionate of formula (I') per 100 pbw of the composition, more typically no isethionate of formula (I'), i.e. 0 pbw isethionate of formula (I') per 100 pbw of the composition.

According to any one of the invention embodiments, the composition of the present invention each comprise, based on 100 pbw of such composition, from 0 to less than 2 pbw of one amidobetaine, such as for example cocamidopropyl betaine.

More typically the composition of the present invention each comprise, based on 100 pbw of such composition, from 0 to less than 1 pbw of amidobetaine (for example cocamidopropyl betaine), and even substantially no amidobetaine, i.e. from 0 to less than 0.1 pbw amidobetaine per 100 pbw of the composition, more typically no amidobetaine, i.e. 0 pbw amidobetaine per 100 pbw of the composition.

According to any one of the invention embodiments, the composition of the present invention may further comprise an electrolyte.

By the term "electrolyte" we mean here ionic salt totally soluble in the composition at the concentrations used.

According to any one of the invention embodiments, the electrolyte of any composition according to the invention can be selected from the group of alkali, and ammonium salts. In particular such electrolyte can be an alkali salt. As non limiting examples, one may cite electrolyte such as NaCl or KCl.

According to any one of the invention embodiments, the electrolyte is present in the composition in a concentration of about 0.2 to 3 pbw relative to the weight of the composition, for instance in a concentration lower than 2.5 pbw.

The composition of the invention may further comprise additional optional ingredients which may bring specific benefits for the intended use. Such optional ingredients may include colorants, pearlescent agents, emollients, hydrating agents, opacifiers, preservatives and pH adjusters. The skilled person is able to select according to general knowledge in the art of formulating personal care compositions such as shampoos, shower gels and liquid hand soaps, and the vast literature there-related, appropriate such optional ingredients for application purposes.

In one embodiment, the composition of the present invention further comprises one or more benefit agents, such as emollients, moisturizers, conditioners, skin conditioners, or hair conditioners such as silicones such as volatile silicones, gums or oils, or non-amino silicones and mixtures thereof, mineral oils, vegetable oils, including arachis oil, castor oil, cocoa butter, coconut oil, corn oil, cotton seed oil, olive oil, palm kernel oil, rapeseed oil, safflower seed oil, sesame seed oil and soybean oil, esters, including butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, animal fats, including acetylated lanolin alcohols, lanolin, lard, mink oil and tallow, and fatty acids and alcohols, including behenic acid, palmitic acid, stearic acid, behenyl alcohol, cetyl alcohol, cicosanyl alcohol and isocetyl alcohol; vitamins or their derivatives, such as vitamin B complex, including thiamine, nicotinic acid, biotin, pantothenic acid, choline, riboflavin, vitamin B6, vitamin B12, pyridoxine, inositol, carnitine, vitamins A,C,D,E,K and their derivatives, such as vitamin A palmitate, and pro-vitamins, e.g., panthenol (pro vitamin B5), panthenol triacetate and mixtures thereof; antioxidants; free-radical scavengers; abrasives, natural or synthetic; dyes; hair coloring agents; bleaching agents; hair bleaching agents; UV absorbers, such as benzophenone, bornelone, PABA (Para Amino Benzoic Acid), butyl PABA, cinnamidopropyl trimethyl ammonium chloride, disodium distyrylbiphenyl disulfonate, potassium methoxycinnamate; anti-UV agents, such as butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, octyl dimethyl PABA (padimate O), red petrolatum; antimicrobial agents; antibacterial agents, such as bacitracin, erythromycin, triclosan, neomycin, tetracycline, chlortetracycline, benzethonium chloride, phenol, parachlorometa xylenol (PCMX), triclocarban (TCC), chlorhexidine gluconate (CHG), zinc pyrithione, selenium sulfide; antifungal agents; melanin regulators; tanning accelerators; depigmenting agents, such as retinoids such as retinol, kojic acid and its derivatives such as, for example, kojic dipalmitate, hydroquinone and its derivatives such as arbutin, transexamic acid, vitamins such as niacin, vitamin C and its derivatives, azelaic acid, placertia, licorice, extracts such as chamomile and green tea, where retinol, kojic acid, and hydroquinone are preferred; skin lightening agents such as hydroquinone, catechol and its derivatives, ascorbic acid and its derivatives; skin-coloring agents, such as dihydroxyacetone; liporegulators; weight-reduction agents; anti-acne agents; antiseborrhocic agents; anti-ageing agents; anti-wrinkle agents; keratolytic agents; anti-inflammatory agents; anti-acne agents, such as tretinoin, isotretinoin, motretinide, adapalene, tazarotene, azelaic acid, retinol, salicylic acid, benzoyl peroxide, resorcinol, antibiotics such as tetracycline and isomers thereof, erythromycin, anti-inflammatory agents such as ibuprofen, naproxen, hetprofen, botanical extracts such as alnus, arnica, artemisia capillaris, asiasarum root, calendula, chamomile. Cnidium, comfrey, fennel, galla rhois, hawthorn, houttuynia, hypericum, jujube, kiwi, licorice, magnolia, olive, peppermint, philodendron, salvia, sasa albomarginata, imidazoles such as ketoconazole and clubiol, those anti-acne agents described in Gollnick, H. et al. 196(1) Dermatology Sebaceous Glands, Acne and Related Disorders, 119-157 (1998), which is incorporated by reference herein to the extent that it is not inconsistent with the present application; refreshing agents; cicatrizing agents; vascular-protection agents; agents for the reduction of dandruff, seborrheic dermatitis, or psoriasis, such as zinc pyrithione, shale oil and derivatives thereof such as sulfonated shale oil, selenium sulfide, sulfur, salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, ciclopirox olamine, anti-psoriasis agents such as vitamin D analogs, e.g. calcipotriol, calcitriol, and tacalcitrol, vitamin A analogs such as esters of vitamin A including vitamin A palmitate, retinoids, retinols, and retinoic acid, corticosteroids such as hydrocortisone, clobetasone, butyrate, clobetasol propionate; antiperspirants or deodorants, such as aluminum chlorohydrates, aluminum zirconium chlorohydrates; immunomodulators; nourishing agents; depilating agents, such as calcium thioglycolate, magnesium thioglycolate, potassium thioglycolate, strontium thioglycolate; agents for combating hair loss; reducing agents for permanent-waving; reflectants, such as mica, alumina, calcium silicate, glycol dioleate, glycol distearate, silica, sodium magnesium fluorosilicate; essential oils and fragrances.

In one embodiment, the composition of the present invention comprises a benefit agent selected from insoluble or partially insoluble ingredients such as moisturizers or conditioners, hair coloring agents, anti-UV agents, anti-wrinkle agents, fragrances or essential oils, skin-coloring agents, anti-dandruff agents, and provides enhanced deposition of such benefit agent on the substrate, ex. Hair and/or skin or fabric or counter top or plant leaves.

In one embodiment, the personal care composition of the present invention further comprises from about 0.1 to about 50 pbw, more typically from about 0.3 to about 25 pbw, and still more typically from about 0.5 to 10 pbw, of one or more benefit agents.

The composition according to the present invention may optionally further comprise other ingredients, such as, for example, preservatives such as benzyl alcohol, methyl paraben, propyl paraben, imidazolidinyl urea, sodium benzoate, potassium sorbate, salicylic acid, methylchloroisothiazolinone and methylisothiazolinone, thickeners such as high molecular weight crosslinked polyacrylic acid (carbomer), PEG diester of stearic acid and the like, and viscosity modifiers such as block polymers of ethylene oxide and propylene oxide, electrolytes, such as sodium chloride, sodium sulfate, and polyvinyl alcohol, pH adjusting agents such as citric acid, succinic acid, phosphoric acid, sodium hydroxide, and sodium carbonate, perfumes, dyes, and sequestering agents, such as disodium ethylenediamine tetra-acetate. In general, personal care compositions may optionally comprise, based on 100 pbw of the personal care composition and independently for each such ingredient, up to about 10 pbw, preferably from 0.5 pbw to about 5.0 pbw, of such other ingredients, depending on the desired properties of the personal care composition.

In general, a composition of the present invention may optionally comprise, based on 100 pbw of the personal care composition and independently for each such ingredient, up to about 15 pbw, preferably from 0.5 pbw to about 10 pbw, of such other ingredients, depending on the desired properties of the composition.

The composition of the present invention is used in a manner know in the art, for example, in the case of a cleanser or shampoo, by application of the cleanser or shampoo to the skin and/or hair and optionally rinsing the cleanser or shampoo off of the skin and/or hair with water.

According to any one of the invention embodiments, the composition of the invention may have a pH comprised between 4 and 11.

According to any one of the invention embodiments, the composition of the invention may be prepared using a concentrated flowable surfactant composition.

The invention is also directed toward concentrates that are suitable to prepare a composition of the invention.

Concentrates including a mixture of surfactants and/or conditioning agents are advantageous as their use would reduce the need to transport a plurality of individual components.

Personal care compositions are usually prepared by mixing individual surfactants and conditioning agents. These components may be supplied as concentrated solutions which are diluted and/or and combined in appropriate ratios by the formulator. The invention covers any surfactant concentrate to be used as component ingredient to prepare a composition of the invention, and especially to surfactant concentrates containing limited levels of water (more advantageous from a cost and environmental perspective).

EXAMPLES

The invention will now be described in further detail by way of the following non limiting examples, wherein the abbreviations have the usual meaning in the art. The temperatures are indicated in degrees centigrade (° C.) and the other parameters in the respective current units. Water amount indicated as "q.s." are intended to be "the amount required to complete to 100%".

Example 1

The following sulfate-free shampoo compositions were prepared.

The starting materials used are identified by the INCI names and/or by the commercial references. All ingredients are expressed by weight percent of the total formulation and as level of active ingredients.

| | Formulation 1 | Comparative Formulation 1a | Comparative Formulation 1b |
|---|---|---|---|
| Mackanate ® EL (Disodium Laureth Sulfosuccinate) | 6.0 | 6.0 | 6.0 |
| Miranol ® Ultra L32 (Sodium Lauroamphoacetate) | 3.0 | — | 3.0 |
| Mackam ® CAB-818 (Cocamidopropyl betaine) | — | 3.0 | — |
| Pureact ® I-78C (Sodium Cocoyl Isethionate) | 2.5 | 2.5 | 2.5 |
| Geropon ® T-77 (Sodium Methyl Oleoyl Taurate) | 1.5 | 1.5 | 1.5 |
| Mackamide ® CPA (Cocamide MIPA) | 1.5 | 1.5 | 1.5 |
| Jaguar ® LS (Hydroxypropyl guar hydroxy-propyltrimonium chloride) | 0.4 | 0.4 | — |
| Jaguar ® C14S (guar hydroxy-propyltrimonium chlroide) | — | — | 0.4 |
| Carbobol ® Ultrez 10 (carbomer) | 0.4 | 0.4 | 0.4 |
| Xiameter ® MEM-1664 (Dimethicone, Laureth-4, Laureth-23) | 2.0 | 2.0 | 2.0 |
| De-ionized water | Up to 100 | Up to 100 | Up to 100 |
| Citric acid solution (50%) | q.s | q.s | q.s |
| Sodium hydroxide solution (15%) | q.s | q.s | q.s |
| Kathon ® CG (Methyl-chloroisothiazolinone, Methylisothiazolinone) | 0.05 | 0.05 | 0.05 |
| Sodium Chloride | 0.45 | 1.93 | 0.51 |
| pH | 5.6 | 5.35 | 5.4 |
| Brookfield Viscosity at 10 RPM, RV spindle 4 (mPa · s) | Between 7,000 and 10,000 | Between 7,000 and 10,000 | Between 7,000 and 10,000 |

Formulation Procedure

Add 27 parts of de-ionized water in a tared beaker A under continuous stirring and heat at 65° C. Add Mackamide® CPA and mix at 100 RPM. After 10 minutes, add Pureact®I-78C followed by Geropon® T-77 and let under stirring during 30 minutes. Stop heating and let the mixture under stirring until it comes back at 30° C. If necessary, compensate for water loss that has occurred during heating step.

In another beaker B, prepare a 10 wt % dispersion in water of Jaguar® LS (or Jaguar® C14S).

In the main vessel, charge 27 parts of DI water for 100 parts of formulation and add Carbopol® Ultrez 10 without stirring. Let it fully disperse in water during a few minutes. Then, add a few drops of a solution of sodium hydroxide (15%) under gentle stirring up to pH 5, and stir until the mixture becomes viscous & transparent. Add slowly Mackanate EL under gentle stirring. Adjust pH between 5.0 and 5.5 with a solution of sodium hydroxide (15%). Add Mackam® CAB 818 (or Miranol® Ultra L32). Add beaker B into the main vessel and stir during 5 minutes. Add the pre-mix of beaker A into the main vessel under continuous stirring at 100 RPM during 10 minutes.

Add Xiameter® MEM-1664 under continuous stirring,. Adjust final pH between 5.0 and 6.0 with a solution of citric acid or sodium hydroxide), add Kathon®CG followed by sodium chloride addition to achieve a targeted Brookfield Viscosity between [7000-10000 mPa·s] at 10 RPM and add de-ionized water up to 100 parts.

Viscosity Measurement

The viscosity of each composition was measured after 24-hours in a temperature-controlled room (21±3° C.), using a Brookfield Viscosimeter Model DV-II+ at 10 RPM, with a RV spindle 4 or 5. The viscosity value was always taken after a stabilization time of 1 min.

Performances

Viscosity of each formulation has been adjusted with added salt (sodium chloride) to yield formulations having a similar viscosity within a satisfactory range (between 7,000 and 10,000 cps).

In this viscosity range the performances of Formulation 1 (which includes the particular combination of lauramphoacetate and sulfosuccinate together with a specific derivatized cationic guar in accordance with the invention) have been compared to the performances of Comparative Formulation 1a and 1b, in terms of conditioning (silicone deposition), foam volume and foam % humidity, according to the following methodologies.

Silicone Deposition Measurement on Hair Tresses

The deposition efficiency of shampoos was measured on calibrated Virgin Medium Brown Caucasian Hair (hair tress weight: 4.0 grams; width: 2.5 cm and length below epoxy glue clip: 17 cm) purchased from IHIP (International Hair Importers & Products Inc.).

The method contains 4 steps: the pre-treatment of the hair tresses with a 10% SLES (sodium lauryl ether sulfate) solution, the treatment of the hair tresses with the shampoo, the dimethicone extraction using 2-Methyl THF (Tetrahydrofuran) and the dosage of the extracted dimethicone using GPC.

Hair Tress pre-Treatment

Hair tresses were pre-treated with a 10% SLES solution, then rinsed with water prior to treatment with the dimethicone-containing shampoo. The procedure was as follows: each tress was put under a controlled water flow (150 mL/min at 38° C.) for 1 minute, then 3 mL of a 10 wt % SLES solution was applied along the hair tress. Finally, the hair tress was rinsed under running water for 1 minute.

Hair Treatment

Approximately 400 mg of shampoo were weighed out precisely. The hair tress was rolled around the finger and the shampoo was withdrawn with it. Then, the product was massaged into the hair for 45 s, and precaution was taken to be sure that the product was distributed evenly across the tress assembly. The hair tress was then rinsed under running water for 30 s. The excess water was stripped off from the tress by pulling through middle finger and forefinger and the hair tress was left to dry and equilibrate overnight in a climatic room (21° C., 50% H.R.)

Silicone Extraction

For each hair tress, 100 ml polyethylene bottles were tarred. The hair tress was introduced in the bottle while maintaining the mounting tab outside the bottle. The hair was cut just below the mounting tab and the amount of hair introduced in the bottle was recorded. Then, about 35 ml of 2-Methyl THF were introduced in each of the polyethylene bottles, before capping them. All the bottles were placed on the agitation table and left to mix for 3 hours at 200 rpm. Under the hood, the THF extraction solution was transferred in a 150 ml evaporating dish and left to evaporate (maximum ventilation rate) for 1 night under the hood.

Dosage of the Extracted Dimethicone

The evaporating dish capped was tarred with a watch glass. Under the hood, about 3 ml of THF were introduced in the evaporating dish. Using a spatula, the dimethicone deposited onto the walls of the evaporating dish was re-dissolved. Once the silicone was re-solubilized, the evaporating dish capped was weighed with the watch glass and the amount of THF introduced was recorded. Using a syringe, the dimethicone solution was transferred in a 2 ml vial and the vial was capped. The dimethicone concentration was dosed in the vial using GPC. The amount of dimethicone deposited on hair, Q, expressed in ppm (µg of dimethicone per gr of hair) was calculated as follows:

$$Q(\mu\text{g dimethicone per gram of hair}) = \frac{C_{dimethicone} \times m_{THF}}{m_{hair}}$$

where Cdimethicone is the dimethicone concentration in the GPC vial expressed in ppm (µg dimethicone per gram of THF), mTHF the amount of THE, expressed in grams, used to re-solubilize the dimethicone in the evaporating dish and mhair, the amount of hair expressed in grams introduced in the polyethylene bottle. The deposition yield was calculated as follows:

$$R(\%) = \frac{C_{dimethicone} \times m_{THF}}{m_{shampoo} \times \phi}$$

where mshampoo is the amount of shampoo, expressed in micro-grams, used to treat the hair tress andφ, the concentration of dimethicone in the shampoo. A minimum of 3 hair tresses were used for each formulation to calculate an average amount of silicone deposited on hair and an average deposition yield.

Results of silicone deposition measurement on hair tresses were the following:

| Composition reference | Cationic Guar | Amphoteric surfactant | Average deposition µg/gr of hair | Silicone Deposition Yield (%) |
|---|---|---|---|---|
| Formulation 1 | Jaguar LS | Sodium Lauroamphoacetate | 634 | 30.5 |
| Comparative Formulation 1a | Jaguar LS | Cocamido-propylbetaine | 509 | 24.7 |
| Comparative Formulation 1b | Jaguar C14S | Sodium Lauroamphoacetate | 409 | 19.8 |

The composition combining a lauramphoacetate and a derivatized cationic guar in accordance of the invention provides significantly higher conditioning on hair, as demonstrated by the silicone deposition measurement on hair tresses, compared to comparative compositions containing a different amphoteric surfactant (Comparative Formulation 1a) or a different cationic guar (Formulation 1b).

Example 2

The following sulfate-free shampoo compositions were prepared.

The starting materials used are identified by the INCI names and/or by the commercial references. All ingredients are expressed by weight percent of the total formulation and as level of active ingredients.

| | Comparative Formulation 2 | Formulation 2 |
|---|---|---|
| Mackanate ® EL (Disodium Laureth Sulfosuccinate) | 6.0 | 6.0 |
| Miranol ® Ultra L32 (Sodium Lauroamphoacetate) | — | 4.0 |
| Mackam ® CAB-818 (Cocamidopropyl betaine) | 4.0 | — |
| Pureact ® I-78C (Sodium Cocoyl Isethionate) | 2.0 | 2.0 |
| Geropon ® T-77 (Sodium Methyl Oleoyl Taurate) | 1.8 | 1.8 |
| Mackamide ® CPA (Cocamide MIPA) | 1.5 | 1.5 |
| Jaguar ® LS (Hydroxypropyl guar hydroxypropyltrimonium chloride) | 0.4 | 0.4 |
| Citric acid solution (50%) | q.s | q.s |
| sodium chloride | 2.0 | 0.33 |
| Kathon ® CG (Methylchloroisothiazolinone, Methylisothiazolinone) | 0.05 | 0.05 |
| De-ionized water | up to 100 | up to 100 |
| pH | 5.4 | 5.6 |
| Brookfield Viscosity at 10 RPM (mPa · s) (RV spindle 4) | Between 7,000 and 10,000 | Between 7,000 and 10,000 |

Formulation Procedure

Add 27 parts of de-ionized water in a tared beaker A under continuous stirring and heat at 65° C. Add Mackamide® CPA and mix at 100 RPM. After 10 minutes, add Pureact®I-78C. After 5 minutes add of Geropon® T-77 and let under stirring during 30 minutes. Stop heating and let the mixture under stirring until it comes back at 30° C. If necessary, compensate for water loss that has occurred during heating step.

In another vessel, charge 30 parts of de-ionized water. Add Jaguar LS in the vessel and adjust pH at 5.5 with a 50% solution of citric acid, under stirring, until the solution becomes clear. Add Miranol® Ultra L32 (or Mackam® CAB 818) under stirring, followed by Mackanate® EL. Add the pre-mix of beaker A into the main vessel under continuous stirring at 100 RPM during 10 minutes. Add sodium chloride up to achieve a targeted viscosity of [7000-10000 mPa·s] at 10 RPM and adjust pH at 5.5±0.2 with a 50% solution of citric acid under continuous stirring. Add Kathon®CG and add de-ionized water up to 100 parts.

Performances

Viscosity of each formulation has been adjusted with added salt (sodium chloride) to yield formulations having a similar viscosity within a satisfactory range (between 7,000 and 10,000 cps).

In this viscosity range the performances of Formulation 2 (which includes the particular combination of lauramphoacetate and sulfosuccinate together with a specific derivatized cationic guar in accordance with the invention) has been compared to the performances of Comparative Formulation 2, in terms of sensorial assessment on hair tresses, foam volume and foam % humidity, according to the following methodologies.

Sensorial Assessment on Hair Tresses

Flat Calibrated tresses of virgin (medium brown) or bleached Caucasian hair, weighing about 10 grams, length of hair: 21 cm below clip and 3 cm width were used. They were purchased from Kerling International Haarfabik GmbH, Donaustr. 7, D-71522 Backnang-Waldrems in Germany (for bleached Caucasian hair and from Intenational Hair Importer Product, 87-29 Myrtle Ave., Glendale, NY 11385 form virgin medium brown). Sensorial analysis was performed by a trained expert panellist, following the standardized protocol described below.

Prior to being actually shampooed, the hair tresses were first cleansed with a 10% active sodium laureth sulfate (SLES) solution. Each hair tress was then wetted under flowing tap water (controlled flow 1100 mL +/−40 mL per 10 sec) at controlled temperature (36.5° C.±1° C.) during 1 minute. 1 ml of shampoo formulation was applied over the entire length of the hair tress and foam was produced by massaging the hair tress from the top to the bottom during 1 min 30 sec with one's hand. The speed at which the foam forms after 15 seconds (so-called "flash-foam") was scored (a score of 1 corresponds to a very slow-forming foam; a score of 2, a slow-forming foam; a score of 3, a medium rapid forming foam; a score of 4, a rapid forming foam; a score of 5 a very rapid forming foam).

The foam generated in the hands and on hair tress was then collected in a conic beaker of 250 mL. The amount of foam was assessed and the foam quality attributes were noted (whiteness, density, richness). Then the hair tress was rinsed during 1 min 15 sec, under flowing tap water at controlled flow, with gentle squeezing of the hair tress from roots to tips with the fingers. After rinsing, the excess water was removed by squeezing the hair tress with two fingers, and the time necessary to detangle the hair tress with a wide-tooth comb was monitored.

Sensorial analysis on bleached hair tresses were performed by one expert panellist. Results were the following:

| | Comparative Formulation 2 | Formulation 2 |
|---|---|---|
| flash foam [score 1 (very low)-5 (very high)] | 2.5 | 3.5 |
| Foam volume (ml) | 30 ml | 30 ml |
| Detangling time | 5 min 30 sec | 4 min 54 sec |

Formulation 2 (which includes the particular combination of lauramphoacetate and sulfosuccinate together with a specific derivatized cationic guar in accordance with the invention) exibit overall better performances (in terms of speed of foam formation, foam volume and time necessary to achieve hair tress detangling) compared to Comparative Formulation 2.

Foam Volume and Foam % Humidity Methodology

Foam volumes (initial, after 30 sec, 1 minute, 3 minutes and 5 minutes ageing) were measured using a high throughput methodology adapted from Ross-Miles tests. 10-times dilute solutions are prepared by mixing 15 gr of each formulation with 135 gr of deionized water. These diluted formulas are then split as follows: 20 mL are placed into plastic syringes set on a fixed metallic bar. Above the latter, a mobile bar pushes and empties the seringes at controlled speed. The liquids then fall into 100 mL glass cylinders containing 10 mL of the same dilute formulas. The high speed falling jets will create foam which will be photographed as a function of time. When the last drop of the 20 ml diluted solution in the seringe has fallen into glass cylinder, the chronometer and camera are started and the initial foam volume is stated. This parameter as well as the volume of total liquid in glass cylinder is then recorded that after 30 sec, 1 minute, 3 minutes and 5 minutes. The % of humidity at a time (t) in foam is defined as following:

$$\%\ \text{humidity}(t)\text{: }(30-\text{volume of liquid in glass cylinder}\,(t)\times 100)/\text{volume of foam}(t)$$

It is usually recognized that a high % of humidity in foam is desirable, as it correlates well with a whiter, richer lather type, in opposition to dry and dull foam for foams having a low % of humidity.

For each formulation tested, 4 replicates were prepared and the average foam volume, drained liquid volume, and average % humidity were calculated.

Results were the following:

Foam Volume

For each formulation evaluated, 4 replicates of foam volume measurements were done and the average foam volume was calculated from these 4 values.

| Time (sec) | Foam volume (ml) | |
|---|---|---|
| | Comparative Formulation 2 | Formulation 2 |
| 0 | 74.4 | 78.9 |
| 30 | 70.5 | 76.5 |
| 60 | 67.0 | 74.0 |

-continued

| | Foam volume (ml) | |
|---|---|---|
| Time (sec) | Comparative Formulation 2 | Formulation 2 |
| 180 | 63.6 | 70.1 |
| 300 | 62.5 | 67.9 |

Foam volume and stability is significantly higher for compositions of the invention containing sodium lauroamphoacetate, than for a comparative composition containing cocamidopropylbetaine.

Foam % Humidity

The volume of liquid drained (corresponding to the volume of liquid in glass cylinder) was measured by one expert panellist after 30 sec, 1 min, 3 min, 5 min and % humidity of foam generated after 30 sec, 1 min, 3 min, 5 min was calculated as explained above:

| | Comparative Formulation 2 | | Formulation 2 | |
|---|---|---|---|---|
| Time (sec) | % humidity in foam | Volume liquid drained (ml) | % humidity in foam | Volume liquid drained (ml) |
| 30 | 13.5 | 20.5 | 14.4 | 19.0 |
| 60 | 10.4 | 23.0 | 11.5 | 21.5 |
| 180 | 5.7 | 26.4 | 7.0 | 25.1 |
| 300 | 4.0 | 27.5 | 4.6 | 26.9 |

The % of humidity in foam generated by the compositions of the invention containing sodium lauroamphoacetate is significantly higher compared to a comparative composition containing cocamidopropylbetaine.

All these Examples demonstrate that the compositions according to the invention makes it possible to achieve an acceptable compromise between viscosity of the composition, foaming properties and conditioning.

The invention claimed is:

1. A sulfate-free aqueous personal care composition, wherein the composition is an oil in aqueous phase emulsion, comprising:

i) from about 0.2 pbw to about 15 pbw of a derivatized cationic guar comprising cationic substituent groups and non ionic substituent groups, ii) at least 0.05 pbw of an oil, wherein the oil has a droplet size of at least 0.15 μm, and iii) from about 2 pbw to about 20 pbw of a surfactant system comprising at least:

a) one lauramphoacetate, and b) one sulfosuccinate.

2. The composition of claim 1, wherein the cationic substituent group in said derivatized cationic guar comprises a quaternary ammonium radical.

3. The composition of claim 1, wherein the non ionic substituent group in said derivatized cationic guar comprises a hydroxyalkyl and/or poly(alkyleneoxy) radical.

4. The composition of claim 1, wherein the oil in aqueous phase emulsion is a microemulsion, wherein the microemulsion is transparent.

5. The composition of claim 1, wherein the oil in aqueous phase emulsion is a microemulsion, wherein the microemulsion exhibits a transmittance of at least 90%, at a wavelength of 600 nm.

6. A sulfate-free aqueous personal care composition, wherein the composition is an oil in aqueous phase emulsion, comprising:

i) from about 0.2 pbw to about 15 pbw of a derivatized cationic guar comprising cationic substituent groups and non ionic substituent groups, ii) at least 0.05 pbw of an oil, wherein the oil has a droplet size of greater than 0.15 μm to 100 μm, and iii) from about 2 pbw to about 20 pbw of a surfactant system comprising at least:

one lauramphoacetate, and one sulfosuccinate, wherein the composition comprises from 0 to less than 1 pbw of cocamidopropyl betaine based on 100 pbw of the composition.

7. The composition of claim 6, wherein the cationic substituent group in said derivatized cationic guar comprises a quaternary ammonium radical.

8. The composition of claim 6, wherein the non ionic substituent group in said derivatized cationic guar comprises a hydroxyalkyl and/or poly(alkyleneoxy) radical.

9. The composition of claim 6, wherein the oil in aqueous phase emulsion is a microemulsion, wherein the microemulsion is transparent.

10. The composition of claim 6, wherein the oil in aqueous phase emulsion is a microemulsion, wherein the microemulsion exhibits a transmittance of at least 90%, at a wavelength of 600 nm.

11. A sulfate-free aqueous personal care composition, wherein the composition is an oil in aqueous phase emulsion, comprising:

i) from about 0.2 pbw to about 15 pbw of a derivatized cationic guar comprising cationic substituent groups and non ionic substituent groups, ii) at least 0.05 pbw of an oil, wherein the oil has a droplet size of greater than 0.15 μm to 100 μm, and iii) from about 2 pbw to about 20 pbw of a surfactant system comprising at least:

one lauramphoacetate, and one sulfosuccinate.

12. The composition of claim 11, wherein the cationic substituent group in said derivatized cationic guar comprises a quaternary ammonium radical.

13. The composition of claim 11, wherein the non ionic substituent group in said derivatized cationic guar comprises a hydroxyalkyl and/or poly(alkyleneoxy) radical.

14. The composition of claim 11, wherein the oil in aqueous phase emulsion is a microemulsion, wherein the microemulsion is transparent.

15. The composition of claim 11, wherein the oil in aqueous phase emulsion is a microemulsion, wherein the microemulsion exhibits a transmittance of at least 90%, at a wavelength of 600 nm.

* * * * *